US012590969B2

(12) United States Patent
Hu et al.

(10) Patent No.: US 12,590,969 B2
(45) Date of Patent: Mar. 31, 2026

(54) METHOD AND DEVICE FOR DETECTING UREA

(71) Applicant: INDUSTRIAL TECHNOLOGY RESEARCH INSTITUTE, Hsinchu (TW)

(72) Inventors: Jie-Bi Hu, Zhubei City (TW); Chin-Ping Huang, Hsinchu City (TW); Pei-Hua Yeh, Hsinchu City (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 774 days.

(21) Appl. No.: 17/902,696

(22) Filed: Sep. 2, 2022

(65) Prior Publication Data

US 2024/0094214 A1 Mar. 21, 2024

Related U.S. Application Data

(60) Provisional application No. 63/240,087, filed on Sep. 2, 2021.

(51) Int. Cl.
*G01N 33/62* (2006.01)
*G01N 30/06* (2006.01)
*G01N 30/88* (2006.01)

(52) U.S. Cl.
CPC ............. *G01N 33/62* (2013.01); *G01N 30/06* (2013.01); *G01N 30/88* (2013.01)

(58) Field of Classification Search
CPC ........ G01N 33/62; G01N 30/06; G01N 30/88; G01N 30/72; G01N 30/7233; G01N 2030/067; G01N 2030/201; G01N 2030/8813; Y10T 436/142222; Y10T 436/171538; Y10T 436/24; Y10T 436/25; Y10T 436/25375; Y10T 436/255
USPC ......... 436/93, 108, 161, 164, 172, 173, 174, 436/177, 178; 422/70, 82.05, 82.08, 527
See application file for complete search history.

(56) References Cited

U.S. PATENT DOCUMENTS

| | | | |
|---|---|---|---|
| 3,068,071 A | 12/1962 | Velluz et al. | |
| 3,567,374 A | 3/1971 | Wybenga et al. | |
| 4,543,337 A | 9/1985 | Klotzsch et al. | |
| 2020/0355586 A1 | 11/2020 | Takahashi et al. | |
| 2021/0293765 A1* | 9/2021 | Hu | G01N 21/3103 |

FOREIGN PATENT DOCUMENTS

| | | | |
|---|---|---|---|
| CN | 102353728 A | | 2/2012 |
| CN | 102928530 A | | 2/2013 |
| CN | 103760266 A | | 4/2014 |
| CN | 103954722 A | * | 7/2014 |
| CN | 107703124 A | | 2/2018 |
| CN | 108061708 A | | 5/2018 |
| CN | 109001126 A | | 12/2018 |
| CN | 109406424 A | | 3/2019 |
| CN | 111448454 A | | 7/2020 |
| CN | 112557454 A | | 3/2021 |
| CN | 113219089 A | | 8/2021 |
| EP | 3 056 232 A1 | | 8/2016 |
| JP | 8-192154 A | | 7/1996 |
| JP | 2000-338099 A | | 12/2000 |
| JP | 2003-344379 A | | 12/2003 |
| JP | 2008-292440 A | | 12/2008 |
| JP | 2018-179545 A | | 11/2018 |
| JP | 2019-184436 A | | 10/2019 |
| JP | 2019-191099 A | | 10/2019 |
| JP | 2019-191100 A | | 10/2019 |
| JP | 2020-144066 A | | 9/2020 |
| JP | 2022-45685 A | | 3/2022 |
| TW | 201934998 A | | 9/2010 |
| TW | 201842333 A | | 12/2018 |
| TW | 202120442 A | | 6/2021 |
| TW | M636111 U | | 1/2023 |
| WO | WO 2021/106267 A1 | | 6/2021 |

OTHER PUBLICATIONS

Chinese Office Action and Search Report for Chinese Application No. 202211072470.X, dated Dec. 3, 2024.

Hua, "Determination of Urea in Soils with High-Performance Liquid Chromatography," Experiment Science & Technology, vol. 6, Period 2, 2008, pp. 43-45, with an English abstract.

Xing et al., "Determination of Urea Content in Yellow Rice Wine by High-performance Liquid Chromatography Combined with Fluorescence Detection after Pre-column Derivatisation," Liquor-Making Science & Technology, Tol. 201, No. 3, 2011, pp. 104-106, with an English abstract.

Clark et al., "Determination of urea using high-performance liquid chromatography with fluorescence detection after automated derivatisation with xanthydrol," Elsevier, Journal Of Chromatography A, 2007, pp. 207-213.

Du, Guang-Yu, et al., "Detection of Urea in Swimming Pool Using High-Performance Liquid Chromatography", Chin J of Public Health Eng, Oct. 2015, vol. 14, No. 5, pp. 478-479.

Qi, Zeng, et al., "Determination of ures in canned foods by high performance liquid chromatography-fluorescence detection coupled with precolumn derivation", Chinese Journal of Chromatography, Jan. 2016, vol. 33, No. 1, pp. 80-83.

(Continued)

*Primary Examiner* — Maureen Wallenhorst
(74) *Attorney, Agent, or Firm* — Birch, Stewart, Kolasch & Birch, LLP

(57) ABSTRACT

A method and device for detecting urea are provided. The method for detecting urea includes the following steps. A derivatization reagent reacts with a sample to obtain a mixture, wherein a reaction time period for reacting urea in the sample with the derivatization reagent to form a derivative product is controlled. The derivative product is separated from the mixture. The amount of separated derivative product is analyzed to determine the concentration of urea in the sample.

19 Claims, 5 Drawing Sheets

(56) References Cited

OTHER PUBLICATIONS

Taiwanese Office Action for Appl. No. 111133305 dated Oct. 5, 2023.
Japanese Office Action for Japanese Application No. 2022-140081, dated Jan. 30, 2024, with English translation.
Wang et al., "Simultaneous Detection of Ethyl Carbamate and Urea in Chinese Yellow Rice Wine by HPLC-FLD," Journal of Liquid Chromatography & Related Technologies, vol. 37, No. 1, dated Oct. 16, 2013, pp. 39-47.

* cited by examiner

200

Introducing a derivatization reagent and a sample from a feed element into a reaction element ~202

Reacting the derivatization reagent with the sample in the reaction element to obtain a mixture, wherein a reaction time period for reacting urea in the sample with the derivatization reagent to form a derivative product is controlled ~204

Introducing the mixture into a volume-control element such that the mixture with a fixed volume is subsequently introduced into a separation element ~206

Separating the derivative product from the mixture via the separation element ~208

Analyzing the amount of separated derivative product via an analysis element to determine the concentration of urea in the sample ~210

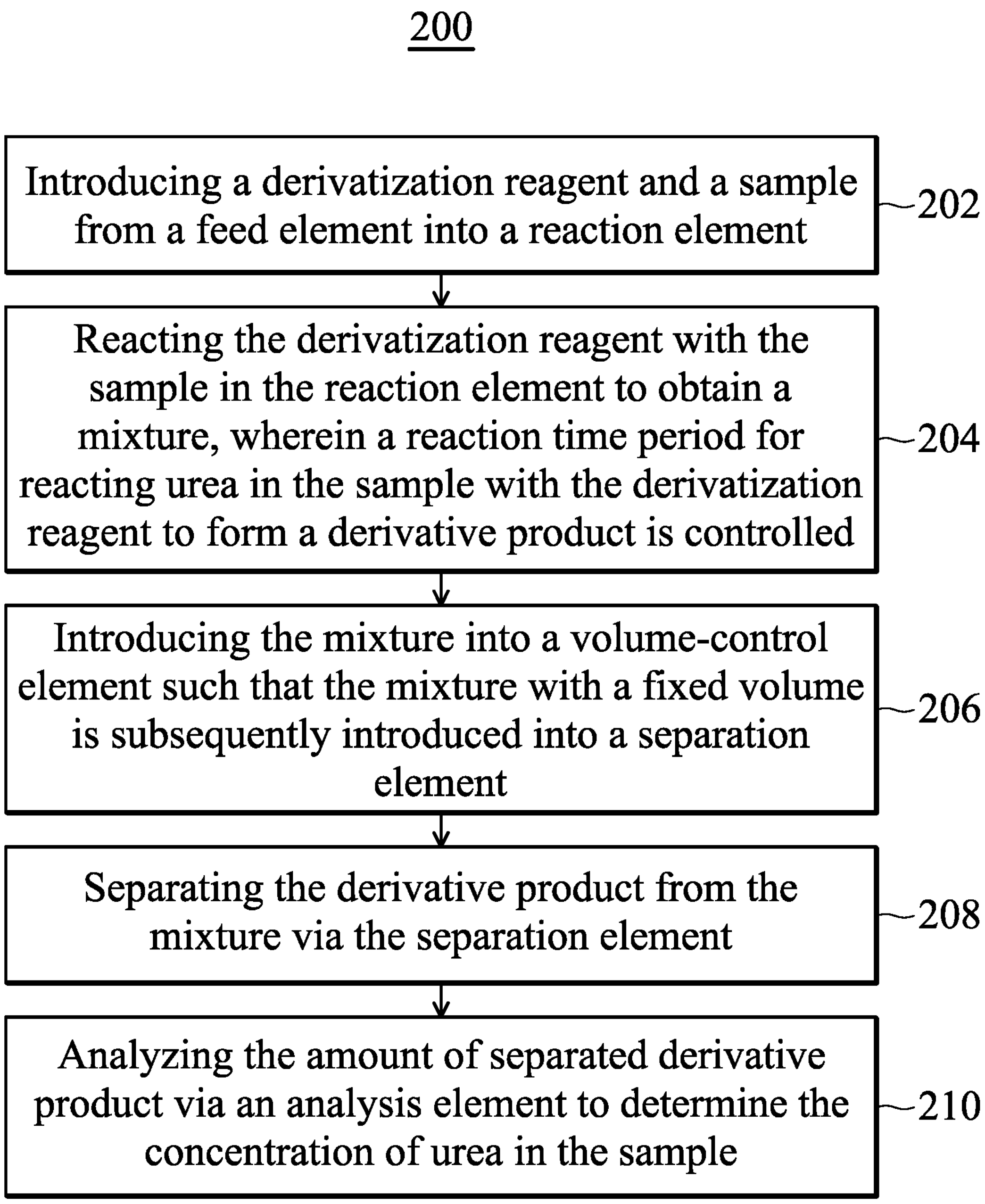

FIG. 5

METHOD AND DEVICE FOR DETECTING UREA

CROSS REFERENCE TO RELATED APPLICATIONS

This application claims the benefit of U.S. Provisional Application No. 63/240,087, filed on Sep. 2, 2021, which is hereby incorporated herein by reference.

TECHNICAL FIELD

The disclosure relates to a method and device for detecting urea.

BACKGROUND

The risk of water shortage is increasing due to environmental change. Industries and governments are working to develop new water sources or recycled water for industrial use. In the wafer manufacturing process, the deep UV immersion lithography process relies on an immersion solution (ultrapure water) to focus the light source. The water quality of ultrapure water (i.e. the amount of organic impurities (such as urea)) will affect the development process, resulting in a T-topping effect which can affect the product process linewidth. The urea content in the ultrapure water used in the process of manufacturing wafers must be carefully monitored to ensure a high wafer yield.

The method of detecting trace amounts of urea in water can be performed by liquid chromatography/mass spectrometry (used in sequential order) (LC-MS/MS) instrumentation for analysis and confirmation, but the aforementioned detection method relies on manual sampling and laboratory analysis, and thus cannot provide real-time urea detection of online samples.

Relevant references proposed that diacetyl monoxime could be used for urea detection. However, the method should be conducted in an environment with a temperature of no lower than 50° C. and not higher than 150° C. Moreover, diacetyl monoxime easily reacts with compounds that are similar to urea, resulting in misinterpretation and inaccurate quantitative urea analyses. In addition, relevant references also proposed the use of xanthydrol to react with urea in acidic environment for quantitative analysis. However, due to the long reaction time and insufficient sensitivity of method that use xanthydrol to react with urea, real-time detection using this method is limited and cannot meet the detection requirements of the semiconductor industry.

Accordingly, novel devices and methods are urgently desired to overcome the problems caused by applying chemical reagents in the online detection of trace urea.

SUMMARY

According to embodiments of the disclosure, the disclosure provides a method for detecting urea. The method for detecting urea includes the following steps. The derivatization reagent reacts with a sample to obtain a mixture. The reaction time period for reacting urea in the sample with the derivatization reagent to form a derivative product is controlled. The derivative product is separated from the mixture. An amount of separated derivative product is analyzed to determine the urea concentration of the sample.

According to embodiments of the disclosure, the disclosure provides a device for detecting urea. The device for detecting urea includes a feeding element, a reaction element, a volume-control element, a separation element, and an analysis element. The feeding element is coupled to the reaction element, such that the derivatization reagent and a sample are introduced into the reaction element using the feeding element, wherein the derivatization reagent reacts with the sample to form a mixture in the reaction element, and the urea in the sample reacts with the derivatization reagent to form a derivative product in the reaction time period. The volume-control element is coupled to the reaction element to introduce the mixture into the volume-control element. The separation element is coupled to the volume-control element, wherein the volume-control element introduces a mixture with a fixed volume into the separation element such that the derivative product in the mixture is separated using the separation element. The analysis element is coupled to the separation element such that an amount of the derivative product is analyzed to the urea concentration of the sample is calculated.

According to some embodiments of the disclosure, the disclosure provides a method for detecting urea which is performed by the aforementioned device for detecting urea. The method for detecting urea includes the following steps. The derivatization reagent reacts with a sample in the reaction element to obtain a mixture, wherein the urea in the sample reacts with the derivatization reagent to form a derivative product in the reaction time period. The mixture is introduced into the volume-control element such that a mixture with a fixed volume is introduced into the separation element. The derivative product is separated from the mixture using the separation element, and the amount of the separated derivative product is analyzed using the analysis element and the urea concentration of the sample is calculated.

A detailed description is given in the following embodiments.

BRIEF DESCRIPTION OF THE DRAWINGS

FIG. 5 is a flow chart illustrating a method 200 for detecting urea according to another embodiment of the disclosure.

DETAILED DESCRIPTION

The method and device for detecting urea are described in detail in the following description. In the following detailed description, for purposes of explanation, numerous specific details and embodiments are set forth in order to provide a thorough understanding of the present disclosure. The specific elements and configurations described in the following detailed description are set forth in order to clearly describe the present disclosure. It will be apparent, however, that the exemplary embodiments set forth herein are used merely for the purpose of illustration, and the inventive concept may be embodied in various forms without being limited to those exemplary embodiments. As used herein, the term "about" in quantitative terms refers to plus or minus an amount that is general and reasonable to persons skilled in the art.

The disclosure provides a method and device for detecting urea. The method for detecting urea of the disclosure includes reacting the derivatization reagent with the urea in the sample to form derivative product and separating the derivative product to perform high-precision qualitative and quantitative detection. The device for detecting urea of the disclosure may employ a reaction element including a reaction control unit (such as microreactor, blender or spoiler) such that the sample reacts with the derivatization reagent to instantly and stably form derivative product.

In addition, the device for detecting urea of the disclosure may employ a separation element (such as chromatographic column) and an analysis element (such as mass spectrometer or optical detection system), thereby overcoming technical problems that the conventional urea detection system cannot be applied to complex water sample (such as municipal wastewater, effluent, influent, well water, or groundwater) and improving detection sensitivity (the urea concentration, which can be detected by the device of the disclosure, in water is from 0 to 300 ppb).

Furthermore, the separation element of the device for detecting urea of the disclosure may include a plurality of chromatographic columns (the chromatographic columns are connected in parallel and disposed in the separation element). Therefore, the separation element is suitable for use in concert with a volume-control element to achieve the technical goal of serial analyzing the derivative product. In addition, when the separation element includes a plurality of chromatographic column, the plurality of chromatographic column may be used interchangeably.

Figure 1:
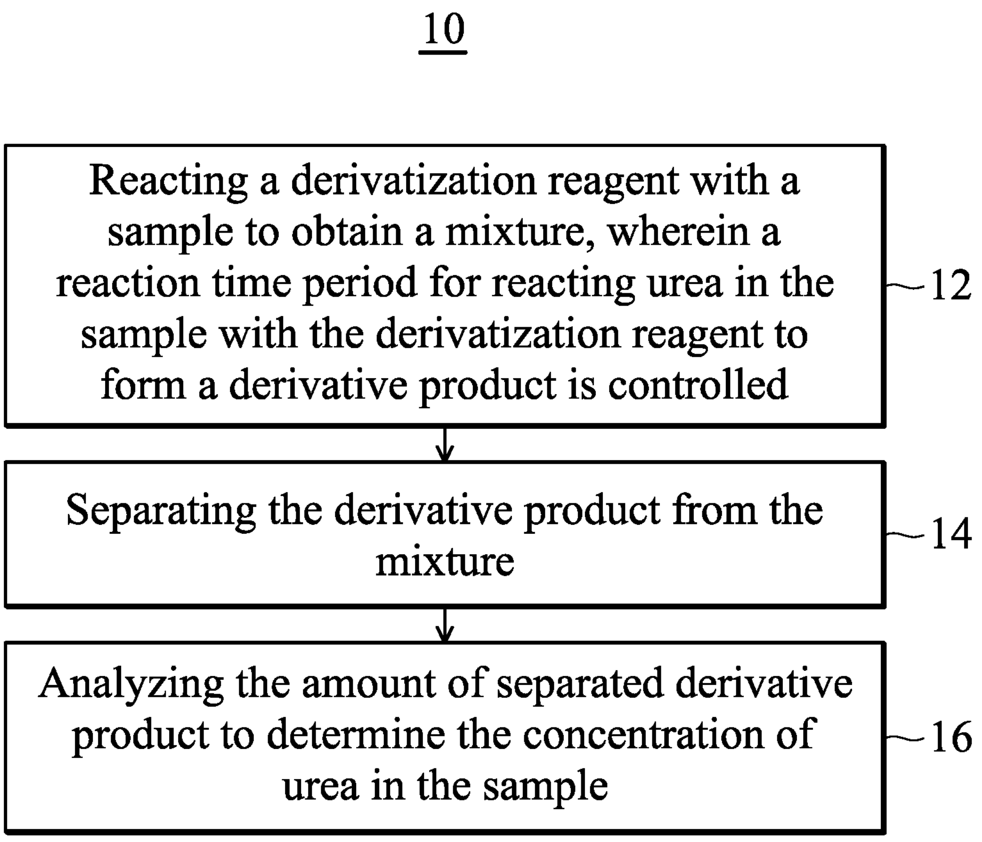
FIG. 1 is a flow chart illustrating a method 10 for detecting urea according to an embodiment of the disclosure.

FIG. 1 is a flow chart illustrating a method 10 for detecting urea according to an embodiment of the disclosure.

The method for detecting urea of the disclosure 10 includes the following steps. First, the derivatization reagent reacts with a sample to obtain a mixture, wherein the reaction time period for reacting urea in the sample with the derivatization reagent to form a derivative product is controlled (steps 12). Next, the derivative product is separated from the mixture (steps 14). Next, an amount of separated derivative product is analyzed to calculate the urea concentration of the sample (steps 16).

According to embodiments of the disclosure, the derivatization reagent can include a reaction product of a compound and an acidic organic solution. According to embodiments of the disclosure, the compound may be xanthydrol, diacetyl monoxime, or a combination thereof. According to embodiments of the disclosure, the acidic organic solution may be hydrochloric acid organic solution, nitric acid organic solution, sulfuric acid organic solution, trifluoroacetic acid organic solution, or a combination thereof. According to embodiments of the disclosure, the concentration of the acidic organic solution may be about 0.05 M to 6 M, wherein the organic solvent used to prepare the acidic organic solution may be various alcohol solvent.

According to embodiments of the disclosure, the concentration of derivatization reagent (i.e. the compound concentration of the derivatization reagent) may be about 0.02 wt % to 0.2 wt %, such as about 0.03 wt %, 0.05 wt %, 0.08 wt %, 0.1 wt %, or 0.15 wt %. If the concentration of the derivatization reagent is too low, the sensitivity of the method for detecting urea would be reduced (i.e. reducing the reactivity between derivatization reagent and urea). If the concentration of the derivatization reagent is too high, the derivatization reagent exhibits poor storability (due to the crystallization).

According to embodiments of the disclosure, the derivatization reagent can include a mixture, wherein the mixture is formed from mixing xanthydrol with acidic organic solution to undergo an acidification. In particular, the amount of xanthydrol may be about 0.02 wt % to 0.2 wt %, based on the total weight of the xanthydrol organic solution.

Figure 2:
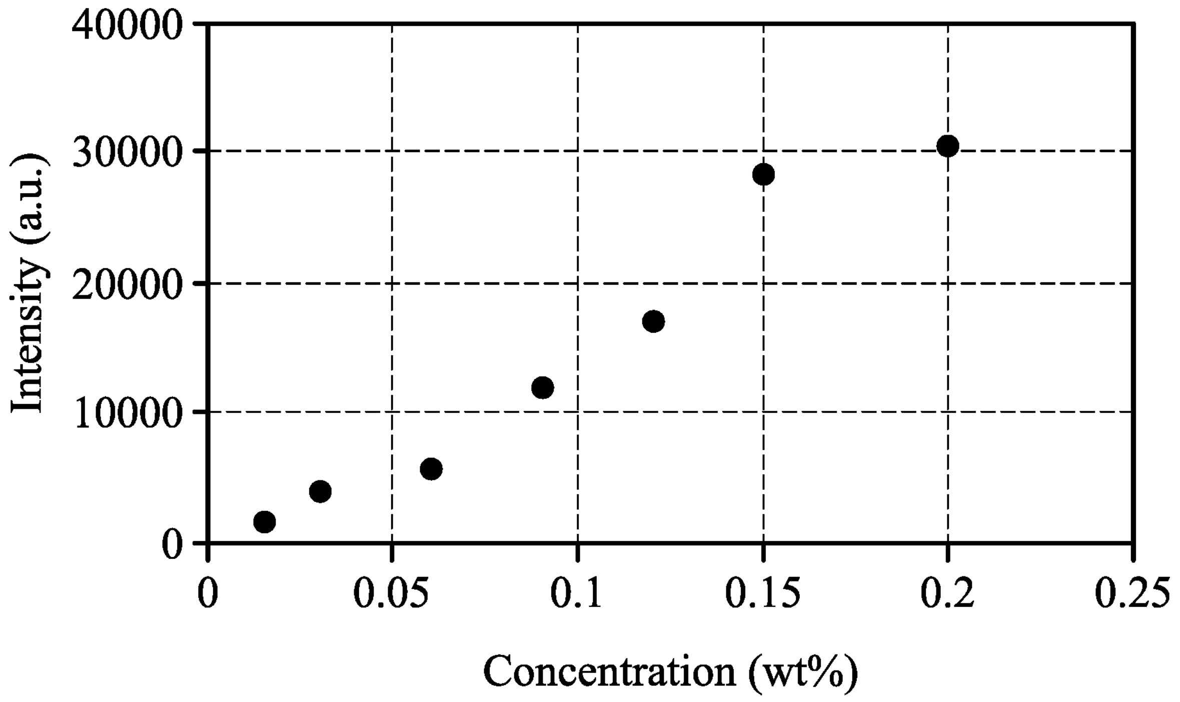
FIG. 2 is a graph plotting the reactivity intensity of derivatization reagent against various concentrations of xanthydrol.

FIG. 2 is a graph plotting the reactivity intensity of derivatization reagent against various concentrations of xanthydrol (the urea concentration of sample is 5 ppb). If the xanthydrol concentration is too low, the sensitivity of the method for detecting urea would be reduced (i.e. reducing the reactivity between derivatization reagent and urea). If the xanthydrol concentration is too high, the derivatization reagent exhibits poor storability (due to the crystallization). The acidification pathway of xanthydrol is as follows:

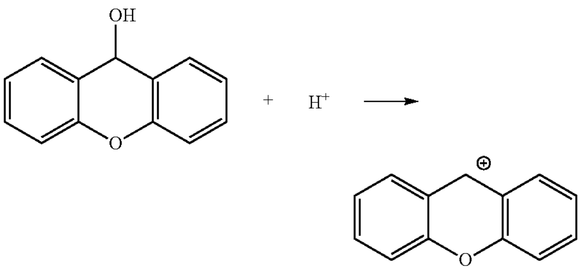

In addition, the reaction pathway for reacting urea with the derivatization reagent to form derivative product is as follows:

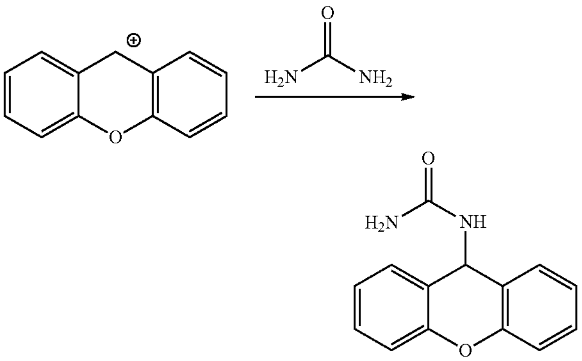

According to embodiments of the disclosure, in the step 12 of the method for detecting urea of the disclosure 10, the reaction between the derivatization reagent and the sample may be optimized (such as raising the reaction temperature, installing spoiler design, increasing the amount of reactor), in order to achieve the purpose for reducing the amount of derivatization reagent and shorten the reaction time period. As a result, the reaction time period for reacting urea in the sample with the derivatization reagent to form a derivative product is controlled, in order to achieve the purpose for rapidly and stably form the derivative product and reduce the formation of by-product. Therefore, the method for detecting urea of the disclosure can be used in real-time urea detection of online sample. According to embodiments of the disclosure, the reaction between the derivatization reagent and the sample may be performed at room temperature. In addition, according to embodiments of the disclosure, the reaction between the derivatization reagent and the sample may be performed at about 25° C. to 40° C. (such as about 30° C. or 35° C.).

According to embodiments of the disclosure, the reaction time period can be controlled in a range from 8 sec to 60 sec (such as 10 sec, 15 sec, 20 sec, 25 sec, 30 sec, 35 sec, 40 sec, 45 sec, 50 sec, or 55 sec). If the reaction time period is too short, the sensitivity of the method for detecting urea would be reduced, and it is easy to lead to the precipitation of side-product (causing pipeline blockage). If the reaction time period is too long, the overall time required for the method for detecting urea would be extended. According to embodiments of the disclosure, the method for detecting urea of the disclosure exhibits high sensitivity (i.e. the urea concentration of sample can be less than 5 ppb) and has the advantage of wide application scope (used to detect a sample with a urea concentration of 0 to 300 ppb).

According to embodiments of the disclosure, the method for separating the derivative product from the mixture may be liquid chromatography. According to embodiments of the disclosure, the amount of the separated derivative product may be detected by fluorescent signal, molecular weight, or ultraviolet absorption signal. According to embodiments of the disclosure, a sample with a known urea concentration may be pre-configured as a standard (reacted with a derivatizing reagent to produce a result with various derivative product) to make a calibration curve, and then the measured signal intensities can be compared with calibration curve to calculate the urea concentration of the sample.

Figure 3:
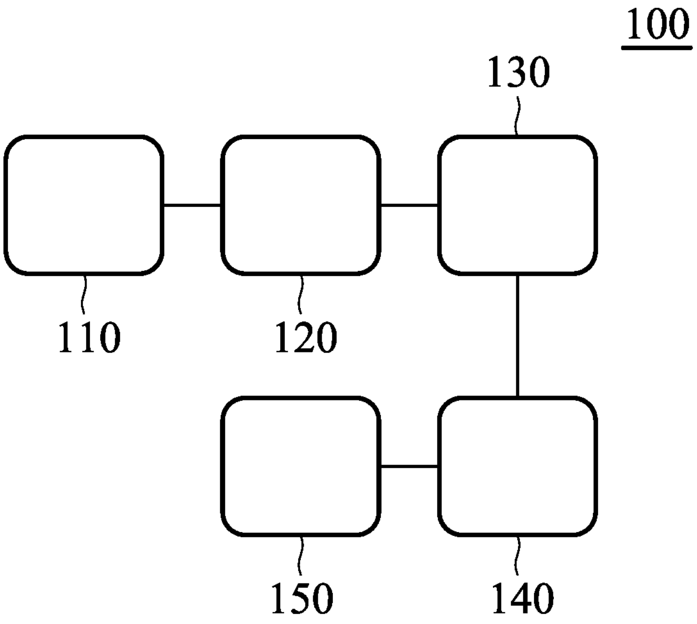
FIG. 3 is a schematic diagram of a device 100 for detecting urea according to an embodiment of the disclosure.

According to embodiments of the disclosure, the disclosure also provides a device for detecting urea. FIG. 3 is a schematic diagram of a device 100 for detecting urea according to an embodiment of the disclosure.

As shown in FIG. 3, the device for detecting urea 100 can include a feeding element 110, a reaction element 120, a volume-control element 130, a separation element 140, and an analysis element 150. According to embodiments of the disclosure, the feeding element 110 is coupled to the reaction element 120, such that the derivatization reagent and the sample are introduced into the reaction element 120 by the feeding unit 110, wherein the derivatization reagent is mixed with the sample in the reaction element 120 to obtain a mixture, and the urea in the sample reacts with the derivatization reagent to form a derivative product for the reaction time period. The volume-control element 130 is coupled to the reaction element 120 to introduce the mixture into the volume-control element 130. The separation element 140 is coupled to the volume-control element 130. The volume-control element 130 can introduce a mixture with a fixed volume into the separation element 140. The derivative product in the mixture is separated from the mixture by the separation element 140. The analysis element 150 is coupled to the separation element 140, such that an amount of the derivative product is analyzed and the urea concentration of the sample is calculated.

According to embodiments of the disclosure, the separation element 140 includes at least one chromatographic column (not shown) and an eluent supply unit (not shown). In addition, according to embodiments of the disclosure, the separation element 140 can include a plurality of (such as at least two) chromatographic columns, and the plurality of chromatographic columns are connected in parallel and disposed in the separation element. As a result, the volume-control element 130 may introduce the mixture with the fixed volume into each chromatographic column in sequence, thereby achieving the technical purpose for serial analyzing the derivative product.

According to embodiments of the disclosure, when the separation element includes a plurality of chromatographic columns, the plurality of chromatographic columns can be used interchangeably. For example, when the separation element includes a first chromatographic column and a second chromatographic column, the first chromatographic column is used to separate the derivative product and the second chromatographic column is washed at the same time.

According to embodiments of the disclosure, the volume-control element 130 includes a multi-port valve (such as six-port valve, or ten-port valve), wherein the multi-port valve may control the connection between the reaction element 120 and the separation element 140 (introducing a mixture with a fixed volume into the chromatographic column) or control the connection between the eluent supply unit and the chromatographic column (introducing the eluent into the chromatographic column to subject to the mixture to a chromatographic analysis). According to embodiments of the disclosure, the analysis element 150 can include a fluorescence spectrometer, mass spectrometer, or UV-visible spectrophotometer.

According to embodiments of the disclosure, the analysis element 150 can include a comparison unit (not shown) in order to compare the signal intensity of the sample with the calibration curve of standard, thereby determining the urea concentration of the sample. According to embodiments of the disclosure, the eluent of the disclosure may be a solvent with high polarity, such as water, alcohol or a combination thereof.

Figure 4:
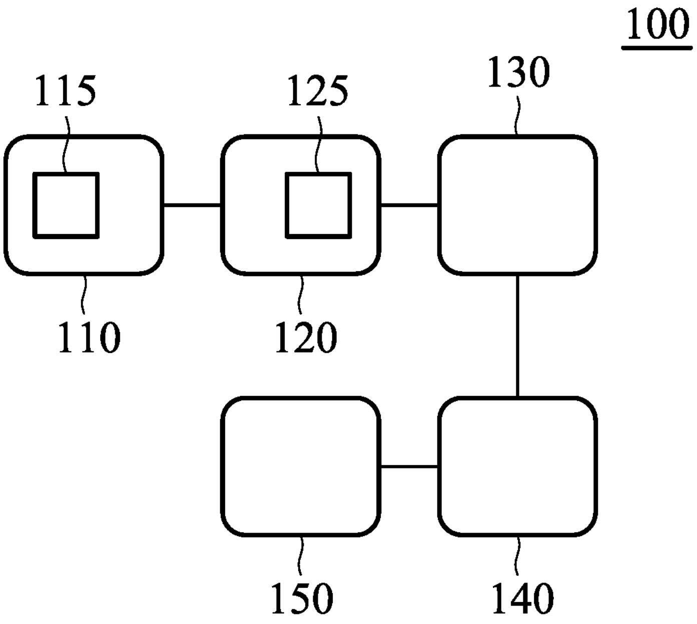
FIG. 4 is a schematic diagram of a device 100 for detecting urea according to another embodiment of the disclosure.

FIG. 4 is a schematic diagram of a device 100 for detecting urea according to another embodiment of the disclosure.

As shown in FIG. 4, a mixing unit 115 may be further disposed in the feeding element 110, wherein a compound is mixed with an acidic organic solution to form the derivatization reagent in the mixing unit 115. In addition, a reaction control unit 125 can be further disposed in the reaction element 120. By means of the reaction control unit 125, the reaction between the derivatization reagent and the sample may be further optimized (such as raising the reaction temperature, installing spoiler design, or increasing the amount of reactor), resulting in that the urea of sample completely reacts with the derivatization reagent to form the derivative product in the reaction time period. According to embodiments of the disclosure, the installing spoiler design may be a reaction coil, wherein the reaction coil has an inner diameter and a length, wherein the inner diameter is between 0.75 mm and 1.2 mm, wherein the length is between about 94 cm and 200 cm. The reaction coil may extend the reaction time period, thereby increasing perturbation to allow that the reaction is mixed well.

According to embodiments of the disclosure, the reaction control unit 125 can include microreactor, blender, spoiler (such as Y-shaped connector, or T-shaped connector), thermostat, or a combination thereof. According to embodiments of the disclosure, the thermostat forces that the derivatization reagent may react with the sample at room temperature or a temperature of 25° C. to 40° C.

According to some embodiments of the disclosure, the disclosure also provides a method for detecting urea 200 which is performed by the device for detecting urea of the disclosure, as shown in FIG. 5. The method for detecting urea includes the following steps. First, the derivatization reagent and the sample are introduced from a feed element 110 into a reaction element 120 (step 202). Next, the derivatization reagent reacts with a sample in the reaction element to obtain a mixture, wherein the reaction time period for reacting urea in the sample with the derivatization reagent to form a derivative product is controlled (step 204). Next, the mixture is introduced into the volume-control element 130 such that a mixture with a fixed volume is introduced into the separation element 140 (steps 206). Next, the derivative product is separated from the mixture using the separation element 140 (steps 208). Next, the amount of the separated derivative product is analyzed by the analysis element 150 to calculate the urea concentration of the sample (steps 210).

According to embodiments of the disclosure, a compound reacts with an acidic organic solution to form the derivatization reagent in a mixing unit 115. According to embodiments of the disclosure, in the step 202 of the method for detecting urea 200 of the disclosure, the reaction between the derivatization reagent and the sample may be further optimized (such as raising the reaction temperature, installing spoiler design, increasing the amount of reactor) using the reaction control unit 125, in order to achieve the purpose for reducing the amount of derivatization reagent and reducing the reaction time period. As a result, the reaction time period for reacting urea in the sample with the derivatization reagent to form a derivative product is controlled, in order to achieve the purpose for rapidly and stably forming the derivative product and reducing the formation of by-product. Therefore, the method for detecting urea of the disclosure can be used in the real-time urea detection of online samples.

According to embodiments of the disclosure, the method for separating the derivative product from the mixture using the separation element 140 may be liquid chromatography. According to embodiments of the disclosure, the amount of the separated derivative product may be determined by fluorescent signal, molecular weight, or ultraviolet absorption signal.

Below, exemplary embodiments will be described in detail so as to be easily realized by a person having ordinary knowledge in the art. The inventive concept may be embodied in various forms without being limited to the exemplary embodiments set forth herein.

EXAMPLES

Example 1

A derivatization reagent (with a concentration of 0.15 wt %) was provided, wherein the derivatization reagent was prepared by reacting xanthydrol with hydrochloric acid organic solution (0.3 M, dissolved in methanol) in a mixing unit of the feeding element. Next, a derivatization reagent and a standard (with a urea concentration of 5 ppb) were introduced into a reaction element via a feeding element, wherein the flow velocity of the derivatization reagent was 16 μL/s, and the flow velocity of the standard was 16 μL/s. Next, the derivatization reagent reacted with the standard in the reaction element to obtain a mixture at a reaction temperature of 35° C., wherein the reaction time period of the reaction between the derivatization reagent and the standard was adjusted using the reaction control unit in the reaction element. Herein, the reaction time period of the reaction between the derivatization reagent and the standard was set at 58.3 sec. Next, the mixture was introduced into the first chromatographic column and the second chromatographic column of the separation element using the volume-control element to perform a separation, obtaining the derivative product. Finally, the obtained derivative product was introduced into the fluorescence spectrometer in the analysis element to perform an analysis, determining the urea concentration after comparison. After repeating the foregoing for 10 times, the relative standard deviation was determined under the reaction time period of 58.3 sec, and the results are shown in Table 1.

Example 2

A derivatization reagent (with a concentration of 0.15 wt %) was provided, wherein the derivatization reagent was prepared by reacting xanthydrol with hydrochloric acid organic solution (0.3 M, dissolved in methanol) in a mixing unit of the feeding element. Next, a derivatization reagent and a standard (with a urea concentration of 5 ppb) were introduced into a reaction element via a feeding element, wherein the flow velocity of the derivatization reagent was 16 μL/s, and the flow velocity of the standard was 16 μL/s. Next, the derivatization reagent reacted with the standard in the reaction element to obtain a mixture at a reaction temperature of 35° C., wherein the reaction time period of the reaction between the derivatization reagent and the standard was adjusted using the reaction control unit in the reaction element. Herein, the reaction time period of the reaction between the derivatization reagent and the standard was set at 34.1 sec. Next, the mixture was introduced into the first chromatographic column and the second chromatographic column of the separation element using the volume-control element to perform a separation, obtaining the derivative product. Finally, the obtained derivative product was introduced into the fluorescence spectrometer in the analysis element to perform an analysis, determining the urea concentration after comparison. After repeating the foregoing for 10 times, the relative standard deviation was determined under the reaction time period of 34.1 sec, and the results are shown in Table 1.

Example 3

A derivatization reagent (with a concentration of 0.15 wt %) was provided, wherein the derivatization reagent was prepared by reacting xanthydrol with hydrochloric acid organic solution (0.3 M, dissolved in methanol) in a mixing unit of the feeding element. Next, a derivatization reagent and a standard (with a urea concentration of 5 ppb) were introduced into a reaction element via a feeding element, wherein the flow velocity of the derivatization reagent was 16 μL/s, and the flow velocity of the standard was 16 μL/s. Next, the derivatization reagent reacted with the standard in the reaction element to obtain a mixture at a reaction temperature of 35° C., wherein the reaction time period of the reaction between the derivatization reagent and the standard was adjusted using the reaction control unit in the reaction element. Herein, the reaction time period of the reaction between the derivatization reagent and the standard was set at 26.6 sec. Next, the mixture was introduced into the first chromatographic column and the second chromatographic column of the separation element using the volume-control element to perform a separation, obtaining the derivative product. Finally, the obtained derivative product was introduced into the fluorescence spectrometer in the analysis element to perform an analysis, determining the urea concentration after comparison. After repeating the foregoing for 10 times, the relative standard deviation was determined under the reaction time period of 26.6 sec, and the results are shown in Table 1.

Example 4

A derivatization reagent (with a concentration of 0.15 wt %) was provided, wherein the derivatization reagent was prepared by reacting xanthydrol with hydrochloric acid organic solution (0.3 M, dissolved in methanol) in a mixing unit of the feeding element. Next, a derivatization reagent and a standard (with a urea concentration of 5 ppb) were introduced into a reaction element via a feeding element, wherein the flow velocity of the derivatization reagent was 16 μL/s, and the flow velocity of the standard was 16 μL/s. Next, the derivatization reagent reacted with the standard in the reaction element to obtain a mixture at a reaction temperature of 35° C., wherein the reaction time period of the reaction between the derivatization reagent and the standard was adjusted using the reaction control unit in the reaction element. Herein, the reaction time period of the reaction between the derivatization reagent and the standard was set at 23.6 sec. Next, the mixture was introduced into the first chromatographic column and the second chromatographic column of the separation element using the volume-control element to perform a separation, obtaining the derivative product. Finally, the obtained derivative product was introduced into the fluorescence spectrometer in the analysis element to perform an analysis, determining the urea concentration after comparison. After repeating the foregoing for 10 times, the relative standard deviation was determined under the reaction time period of 23.6 sec, and the results are shown in Table 1.

Example 5

A derivatization reagent (with a concentration of 0.15 wt %) was provided, wherein the derivatization reagent was prepared by reacting xanthydrol with hydrochloric acid organic solution (0.3 M, dissolved in methanol) in a mixing unit of the feeding element. Next, a derivatization reagent and a standard (with a urea concentration of 5 ppb) were introduced into a reaction element via a feeding element, wherein the flow velocity of the derivatization reagent was 16 μL/s, and the flow velocity of the standard was 16 μL/s. Next, the derivatization reagent reacted with the standard in the reaction element to obtain a mixture at a reaction temperature of 35° C., wherein the reaction time period of the reaction between the derivatization reagent and the standard was adjusted using the reaction control unit in the reaction element. Herein, the reaction time period of the reaction between the derivatization reagent and the standard was set at 13.3 sec. Next, the mixture was introduced into the first chromatographic column and the second chromatographic column of the separation element using the volume-control element to perform a separation, obtaining the derivative product. Finally, the obtained derivative product was introduced into the fluorescence spectrometer in the analysis element to perform an analysis, determining the urea concentration after comparison. After repeating the foregoing for 10 times, the relative standard deviation was determined under the reaction time period of 13.3 sec, and the results are shown in Table 1.

TABLE 1

| reaction stability (at 5 ppb urea) | |
|---|---|
| reaction time period (sec) | relative standard deviation (%) |
| 58.3 | 7.8 |
| 34.1 | 7.8 |
| 26.6 | 6.0 |
| 23.6 | 6.2 |
| 13.3 | 7.7 |

As shown in Table 1, the method for detecting urea of the disclosure can rapidly and stably form derivative product. Therefore, the method for detecting urea of the disclosure can be used in real-time urea detection of online sample.

Comparative Example 1

A derivatization reagent (with a concentration of 0.15 wt %) was provided, wherein the derivatization reagent was prepared by reacting xanthydrol with hydrochloric acid organic solution (0.3 M, dissolved in methanol) in a mixing unit of the feeding element. Next, a derivatization reagent and a standard (with a urea concentration of 5 ppb) were introduced into a reaction element via a feeding element, wherein the flow velocity of the derivatization reagent was 16 μL/s, and the flow velocity of the standard was 16 μL/s. Next, the derivatization reagent reacted with the standard in the reaction element to obtain a mixture at a reaction temperature of 35° C., wherein the reaction time period of the reaction between the derivatization reagent and the standard was adjusted using the reaction control unit in the reaction element. Herein, the reaction time period of the reaction between the derivatization reagent and the standard was set at 4.9 sec. Next, the mixture was introduced into the first chromatographic column and the second chromatographic column of the separation element using the volume-control element to perform a separation, obtaining the derivative product. Finally, the obtained derivative product was introduced into the fluorescence spectrometer in the analysis element to perform an analysis, determining the urea concentration after comparison.

Figure 6:
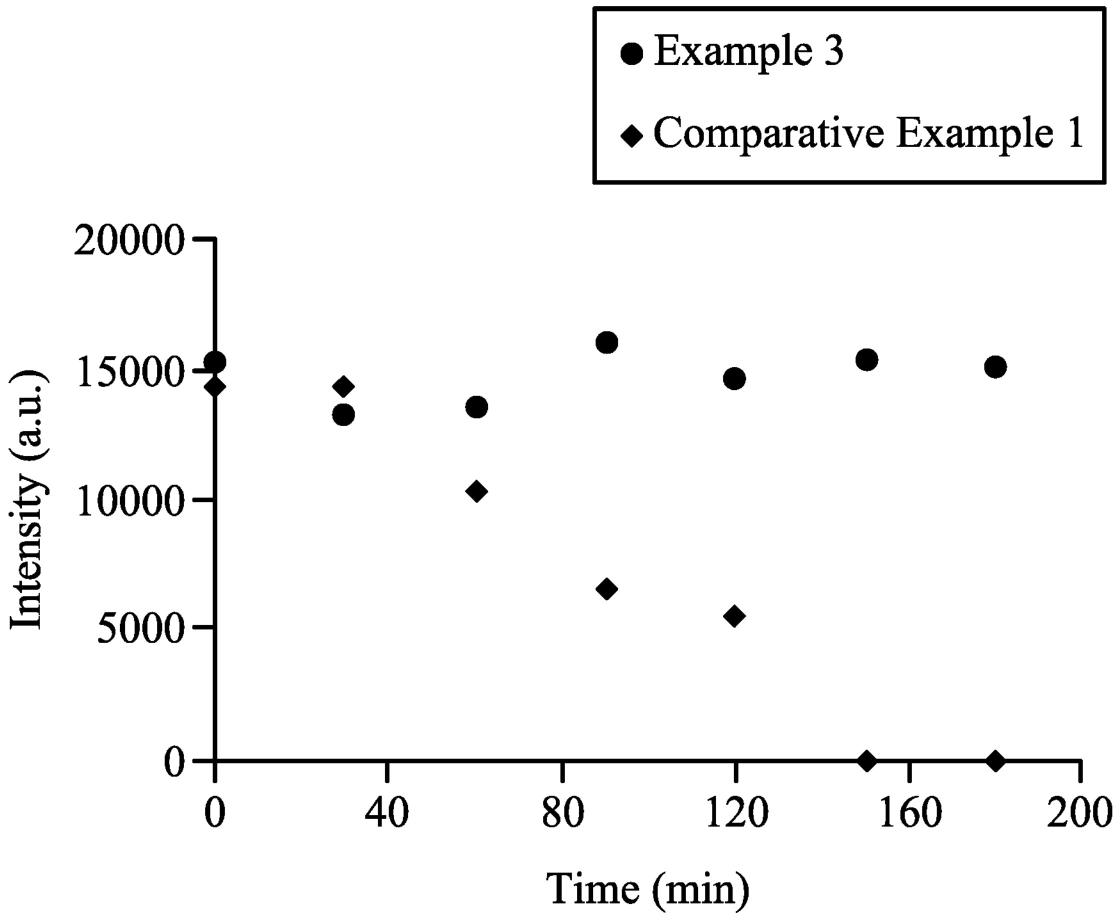
FIG. 6 is a graph plotting the intensity of derivative products, which are measured according to the method for detecting urea in Example 3 or Comparative Example 1, against various time points.

The method for detecting urea as disclosed in Example 3 and Comparative Example 1 were continuously fed and run for 180 minutes after the first measurement, wherein the fluorescence intensity of urea derivative product was measured and recorded every 30 minutes, and the results are shown in FIG. 6.

As shown in FIG. 6, when reducing the reaction time period of the reaction between the derivatization reagent and urea by modifying the reaction control unit, the stability of the method for detecting urea is also reduced.

Example 6

Example 6 was performed in the same manner as Example 3, except that the standard (with a urea concentration of 5 ppb) serving as the sample was replaced with reclaimed water. The urea concentration of reclaimed water was determined after the measurement, and the results are shown in Table 2. In addition, the urea concentration of reclaimed water was measured by the liquid chromatography/mass spectrometry (used in sequential order) (LC-MS/MS) instrumentation, and the results are shown in Table 2.

Example 7

Example 7 was performed in the same manner as Example 3, except that the standard (with a urea concentration of 5 ppb) serving as the sample was replaced with ground water. The urea concentration of ground water was determined after the measurement, and the results are shown in Table 2. In addition, the urea concentration of ground water was measured by the liquid chromatography/mass spectrometry (used in sequential order) (LC-MS/MS) instrumentation, and the results are shown in Table 2.

Example 8

Example 8 was performed in the same manner as Example 3, except that the standard (with a urea concentration of 5 ppb) serving as the sample was replaced with tap water. The urea concentration of tap water was determined after the measurement, and the results are shown in Table 2. In addition, the urea concentration of tap water was measured by the liquid chromatography/mass spectrometry (used in sequential order) (LC-MS/MS) instrumentation, and the results are shown in Table 2.

Example 9

Example 9 was performed in the same manner as Example 3, except that the standard (with a urea concentration of 5 ppb) serving as the sample was replaced with a sample with a methylurea concentration of 5 ppb. The urea concentration of the sample with a methylurea concentration of 5 ppb was determined after the measurement, and the results are shown in Table 2. In addition, the urea concentration of the sample with a methylurea concentration of 5 ppb was measured by the liquid chromatography/mass spectrometry (used in sequential order) (LC-MS/MS) instrumentation, and the results are shown in Table 2.

Example 10

Example 10 was performed in the same manner as Example 3, except that the standard (with a urea concentration of 5 ppb) serving as the sample was replaced with ultrapure water. The urea concentration of ultrapure water was determined after the measurement, and the results are shown in Table 2. In addition, the urea concentration of ultrapure water was measured by the liquid chromatography/mass spectrometry (used in sequential order) (LC-MS/MS) instrumentation, and the results are shown in Table 2.

TABLE 2

| | detected urea concentration (ppb) | |
|---|---|---|
| | device for detecting urea of the disclosure | liquid chromatography/ mass spectrometry (used in sequential order) (LC-MS/MS) |
| reclaimed water | 5.4 | 5.6 |
| ground water | 0.1 | <0.5 |
| tap water | 4.4 | 4.8 |
| sample with a methylurea concentration of 5 ppb | 0.0 | <0.5 |
| ultrapure water | 0.0 | <0.5 |

As shown in Table 2, the device and method for detecting urea of the disclosure can be used to detect trace content of urea in complex water sample and would not be interfered by compound similar to urea Accordingly, the method for detecting urea of the disclosure can form the derivative product by reacting derivatization reagent with urea in the sample, and can qualitatively and quantitatively analyze the separated derivative product with high precision. In addition, the device for detecting urea of the disclosure, which employs the separation element and the analysis element, exhibits improved and can overcome technical problems that the conventional urea detection system cannot be applied to complex water sample.

It will be clear that various modifications and variations can be made to the disclosed methods and materials. It is intended that the specification and examples be considered as exemplary only, with the true scope of the disclosure being indicated by the following claims and their equivalents.

What is claimed is:

1. A method for detecting urea, comprising:

reacting a derivatization reagent with a sample to obtain a mixture, wherein a reaction time period for reacting urea in the sample with the derivatization reagent to form a derivative product is controlled, and wherein a concentration of derivatization reagent is 0.02 wt % to 0.2 wt %;

separating the derivative product from the mixture; and analyzing an amount of separated derivative product to determine a urea concentration of the sample.

2. The method for detecting urea as claimed in claim 1, wherein the derivatization reagent comprises a reaction product of a compound and an acidic organic solution.

3. The method for detecting urea as claimed in claim 2, wherein the compound is xanthydrol, diacetyl monoxime, or a combination thereof.

4. The method for detecting urea as claimed in claim 2, wherein the acidic organic solution is hydrochloric acid organic solution, nitric acid organic solution, sulfuric acid organic solution, trifluoroacetic acid organic solution, or a combination thereof.

5. The method for detecting urea as claimed in claim 1, wherein the urea concentration of the sample is 0 to 300 ppb.

6. The method for detecting urea as claimed in claim 1, wherein the reaction time period is 8 sec to 60 sec.

7. A device for detecting urea, comprising:

a feeding element;

a reaction element coupled to the feeding element such that a derivatization reagent and a sample are introduced into the reaction element using the feeding element, wherein the derivatization reagent is mixed with a sample in the reaction element to obtain a mixture, and a urea in the sample reacts with the derivatization reagent to form a derivative product for a reaction time period, and wherein a concentration of derivatization reagent is 0.02 wt % to 0.2 wt %;

a volume-control element coupled to the reaction element to introduce the mixture into the volume-control element;

a separation element coupled to the volume-control element, wherein the volume-control element introduces the mixture with a fixed volume into the separation element such that the derivative product in the mixture is separated using the separation element; and an analysis element coupled to the separation element such that an amount of the derivative product is analyzed and a urea concentration of the sample is calculated.

8. The device for detecting urea as claimed in claim 7, wherein the feeding element comprises a mixing unit, wherein a compound is mixed with an acidic organic solution in the mixing unit to form the derivatization reagent.

9. The device for detecting urea as claimed in claim 7, wherein the reaction element comprises a reaction control unit to ensure that the derivatization reagent is completely reacted with the urea in the sample to form the derivative product using the reaction control unit in the reaction time period.

10. The device for detecting urea as claimed in claim 9, wherein the reaction control unit comprises a microreactor, mixer, spoiler, thermostat or a combination thereof.

11. The device for detecting urea as claimed in claim 10, wherein the reaction control unit comprises the thermostat, such that the derivatization reagent reacts with the sample at a temperature of 40° C. or lower.

12. The device for detecting urea as claimed in claim 9, wherein the separation element comprises at least one chromatographic column.

13. The device for detecting urea as claimed in claim 12, wherein the separation element comprises at least two chromatographic columns, and the at least two chromatographic columns are connected in parallel and disposed in the separation element.

14. The device for detecting urea as claimed in claim 13, wherein the volume-control element introduces the mixture with the fixed volume into each of the chromatographic columns.

15. The device for detecting urea as claimed in claim 14, wherein the volume-control element comprises a multi-port valve.

16. The device for detecting urea as claimed in claim 7, wherein the analysis element comprises a fluorescence spectrometer, mass spectrometer, or UV-visible spectrophotometer.

17. A method for detecting urea, which is performed by the device for detecting urea as claimed in claim 8, comprising:

reacting the derivatization reagent with a sample in the reaction element to obtain a mixture, wherein the reaction time period for reacting urea in the sample with the derivatization reagent to form a derivative product is controlled;

introducing the mixture into the volume-control element such that a mixture with a fixed volume is introduced into the separation element;

separating the derivative product from the mixture using the separation element; and analyzing an amount of the separated derivative product using the analysis element to determine the urea concentration of the sample.

18. The method for detecting urea as claimed in claim 17, further comprising introducing the derivatization reagent and the sample into the reaction element using the feeding element.

19. The method for detecting urea as claimed in claim 17, wherein the reaction element comprises a reaction control unit such that the urea in the sample is completely reacted with the derivatization reagent to form a derivative product in the reaction time period.

* * * * *